US006628122B2

United States Patent
Newman (10) Patent No.: US 6,628,122 B2
(45) Date of Patent: Sep. 30, 2003

(54) ELECTROSTATIC DISCHARGE TESTING APPARATUS

(76) Inventor: Scott Newman, 14990 SW. Carolwood Dr., Beaverton, OR (US) 97007

( * ) Notice: Subject to any disclaimer, the term of this patent is extended or adjusted under 35 U.S.C. 154(b) by 33 days.

(21) Appl. No.: 10/039,927

(22) Filed: Oct. 26, 2001

(65) Prior Publication Data

US 2003/0080748 A1 May 1, 2003

(51) Int. Cl.[7] .................. G01N 27/00; H01H 31/12; G01R 31/26
(52) U.S. Cl. .................. 324/458; 324/452; 324/701
(58) Field of Search .................. 324/458, 457, 324/452, 454, 455, 693, 695, 696, 701, 724, 456, 558, 559; 209/539

(56) References Cited

U.S. PATENT DOCUMENTS 4,215,306 A * 7/1980 Mace ................... 320/105
4,569,445 A * 2/1986 Kovats et al. ........... 209/539
5,585,730 A * 12/1996 Pazda et al. ............ 324/452
5,760,589 A * 6/1998 Katsuie ................ 324/452
6,166,550 A * 12/2000 Abramsohn et al. ...... 324/452

* cited by examiner

Primary Examiner—John E. Chapman
Assistant Examiner—James C. Kerveros
(74) Attorney, Agent, or Firm—Ipsolon LLP

(57) ABSTRACT

A hand truck like frame has a pair of wheels, each of which is coated with an electrically conductive material so that in a selected operating mode the wheels define electrodes. A separate pair of electrodes is mounted to the frame and the electrodes and the wheels are electrically connected through switching circuits to an ohmmeter. The ESD potential between the electrodes and/or the wheels may be measured in several selected modes for point to point, point to ground and point to bench top measurements.

27 Claims, 4 Drawing Sheets

ELECTROSTATIC DISCHARGE TESTING APPARATUS

FIELD OF THE INVENTION

This invention relates to equipment and methods used in measuring electrical resistance in a worksurface as a prediction for electrostatic discharge potential.

BACKGROUND

Static electricity is commonly defined as an electrical charge resulting from the imbalance of electrons on the surface of a material. Most people are quite familiar with the everyday effects of static electricity—it is the shock one receives when touching a doorknob after walking across a carpet. The technical name for the electrical shock just described is electrostatic discharge (ESD). ESD is technically described as the transfer of electrical charge between bodies—for instance, a human hand and a doorknob—that are at different electrical potentials.

In most everyday situations, ESD can be a bother but rarely a problem. However, the problems resulting from ESD are magnified in industrial settings, where ESD is a major concern. Among the many problems that static discharge can cause are the unintentional ignition of flammable materials, damage to electronic components and systems, and the attraction of contaminants such as charged dust particles in clean room environments. Even centuries ago military forces were aware that ESD could cause the unintentional ignition of black powder. To alleviate this sometimes-catastrophic problem, ESD control measures were used as early as the $14^{th}$ century to protect black powder stores.

Today, many industries—from high tech manufacturing plants to businesses commonly thought of as "smoke stack" industries—are concerned with ESD and its control, since controlling ESD can lead to a safer work environment and reduction or elimination of damage resulting from ESD. While nearly all industries are or should be concerned with controlling ESD, the concern is most acutely felt by businesses in the electronics industry. To give just a few examples of the damage that ESD can cause in the electronics industry, it can destroy or degrade semiconductor devices by changing operational characteristics, it can cause disruptions to the normal operation of an electronic system—sometime leading to equipment failure, and in clean rooms it can cause charged particles to adhere tightly to the surface of a silicon wafer, resulting in distinct problems with wafer production and efficiency.

Given these problems and the economic damage that can result from them, control of ESD is a major concern and a complete industry has grown up around the field of ESD control. Typically, an ESD control program has many different facets, considering for example factors such as the nature of the particular business, product design that takes into account ESD risk factors, defining the level of ESD control needed in the particular setting, identifying areas where ESD control are critical, eliminating sources of ESD generation, dissipating and neutralizing ESD with appropriate techniques, and protecting products from the ESD that will inevitably occur. Although not all industries will need an ESD control program that addresses each of these factors, almost all industries that are concerned with controlling ESD have a need to test their facilities for ESD susceptibility and the effectiveness of control measures.

One critical component of an ESD control program is dissipating and neutralizing ESD with appropriate techniques. As expected, there are many different techniques. One very common protective measure is the use of ESD resistive coatings on worksurfaces such as floors and bench tops. Many highly effective ESD resistive coatings are available for use on floors and other worksurfaces and as a result, nearly all electronics manufacturing facilities use surface coatings of one kind or another. Such coatings are specifically designed to eliminate or minimize the triboelectric charge potential between objects, and have been found to be highly effective.

The effectiveness of the coatings, or the need for coatings in a particular area is determined through ESD testing. The present invention relates to equipment and methods used to test the ESD potential of worksurfaces. Manufacturers routinely test ESD potential as part of an overall ESD control program. Regular testing provides a measure of the need for ESD control measures in a specific work setting, or the ongoing effectiveness of an in-place ESD control device such as a floor of bench top coating.

The level of ESD protection provided by a worksurface is directly related to the time needed to discharge an object. It is known, for example, that the electrical resistance between two points can be correlated to the ESD potential, and electrical resistance values between two points are indicative of the effectiveness of the surface for resisting ESD. Accordingly, worksurface ESD testing focuses on measuring the electrical resistance of flooring materials, packaging materials, bench tops, and point to point and point to ground resistance. While in reality the time that it takes for an object to discharge is related to factors in addition to resistance, such as capacitance, contact resistance and discharge path, it has been found in practice that the resistance measurement provides an effective predictor of the potential for ESD, and through a measurement that is fairly easy to quantify.

Various standards have been developed for measuring the resistance of worksurfaces as a predictor of ESD potential. As an example, ANSI/ESD-S7.1-1994 is an accepted standard for resistive characterization of materials, floor materials. The Electrostatic Discharge Association has also published standards for worksurface resistance measurements at ESD S4.1-1997. These standards are used in many manufacturing facilities.

The equipment used to test worksurface resistivity according to the standards just mentioned is commercially available from various sources. For example, ESD Systems.com (www.esdsystems.com) offers several megohmmeters that are used in compliance with the standards noted above and other published ESD measurement standards. These megohmmeters comprise equipment in compliance with the standards noted and include two 5 lb electrodes, leads and an ohmmeter having appropriate voltage characteristics. In use, the electrodes and ohmmeter are carried to the location where testing is to take place. The electrodes are separated according to the standard specifications—the separation depending upon the type of measurement being taken—and the leads are connected to the ohmmeter. The resistance between electrodes is then measured and the value is used as an indicator of ESD potential, and, for example, the effectiveness of the surface coating. The actual testing routines are spelled out in the appropriate standards.

While the equipment just described complies with the published standards, it can be cumbersome to make the actual measurements on an ongoing basis in the field. For example, the electrodes are relatively heavy and thus difficult to handle. Placing the electrodes on the worksurface at the appropriate separation can be a difficult task, since the separation should be measured with each testing measurement taken to assure compliance with the standard. Moreover, the electrodes are prone to being damaged through repeated use, and the testing method using individual electrodes is necessarily a "batch" operation. That is, resistance measurements are taken at discrete points in a manufacturing facility. While an increase in the number of test locations helps provide a statistical prediction of ESD potential over a larger area of a manufacturing facility, the batch testing routine does not provide a ready method of testing the overall effectiveness of a worksurface other than at discrete test locations.

There is a real need therefore for improved equipment for measuring the resistance of worksurfaces.

The present invention provides an ESD testing apparatus and method that complies with published and industry standard worksurface testing techniques. In a preferred embodiment the present invention comprises a testing apparatus that is mounted on a frame having wheels that allow the unit to be easily moved from location to location for point measurements of worksurface resistance. Electrodes are carried on board the frame and are adjustable to be moved from a first, narrow or retracted position that allows the frame to be easily moved around a manufacturing facility to a second extended position in which the electrodes are spaced at industry standard spacing. The electrodes are capable of measuring resistance in either the retracted or extended positions. The electrodes are removable from mounts on the frame and may be used for point-to-point floor measurements, point to ground measurements, and bench to floor measurements, all according to industry standards.

The present invention further allows for continuous worksurface resistivity testing by measuring resistance values between the frame wheels, which in a selected mode function as the electrodes. The resistance of, for example, a floor surface may thus be measured on a continuous basis as the frame is moved over the floor. This allows for testing of ESD potential and evaluation of ESD risk for a large sample area rather than being limited to multiple single-point test locations, thereby allowing for greater statistical testing and evaluation of ESD risk potential of the surface. To facilitate testing while the device is being rolled over a surface, the wheels are electrically conductive, as for example when the wheels are coated with an electrically conductive material. An electrical connection is made between the conductive coating and an on-board ohmmeter. The wheels are movable between retracted and extended positions to change the spacing between the wheels during testing. In a retracted position the wheels easily fit into tight spaces. In an extended position, the wheels are separated from one another by industry standard spacing.

In one measurement mode, the inventive apparatus may be set to continuously measure the resistance between the wheels as the frame is rolled over the floor. When the frame is tipped into a standing position, a switch may be activated to switch the device into a testing mode using the electrodes rather than the wheels.

The apparatus includes linkage mechanisms for separately moving the electrodes and the wheels from their retracted positions to their extended positions.

The test equipment includes an industry standard ohmmeter in compliance with published standards and standard-compliant electrodes. The ohmmeter is mounted on the frame in a position such that the operator may easily read the test results as the frame is either moved from location to location, or while testing in-transit. The equipment is thus far more ergonomically designed than currently available test equipment. A toolbox is included on the frame to store tools and other supplies that are commonly used during the testing routines.

BRIEF DESCRIPTION OF THE DRAWINGS

The invention will be better understood and its numerous objects and advantages will be apparent by reference to the following detailed description of the invention when taken in conjunction with the following drawings.

DETAILED DESCRIPTION OF THE PREFERRED EMBODIMENTS

Structure

A preferred embodiment of the ESD testing apparatus 10 is shown in FIGS. 1 through 4. Apparatus 10 includes a frame 11 formed of opposite lateral upright frame members 12 and 14, which are interconnected by a handle 16 on the upper ends thereof and by a transverse frame member 18 on the lower ends. A forward extending frame member 20 is connected to an extends from each lateral side of frame member 18, and the forward extending frame members 20 are interconnected by a forward transverse frame member 22. Frame 11 is made of any sufficiently strong material, and is preferably made of heavy gauge aluminum or steel tubing. Fiberglass or composite tubing also may be used to fabricate the frame.

A pair of wheels 24a and 25b is rotatably mounted to a transverse frame member 26 that is mounted to transverse frame member 18. As detailed below, wheels 24a and 24b are movable between a first, retracted position, illustrated in FIG. 1 with the solid lines, and a second, extended position illustrated in FIG. 1 with dashed lines. Accordingly, the wheels are mounted to frame member 26 in a manner to allow each wheel to be moved between these positions.

Figure 1:
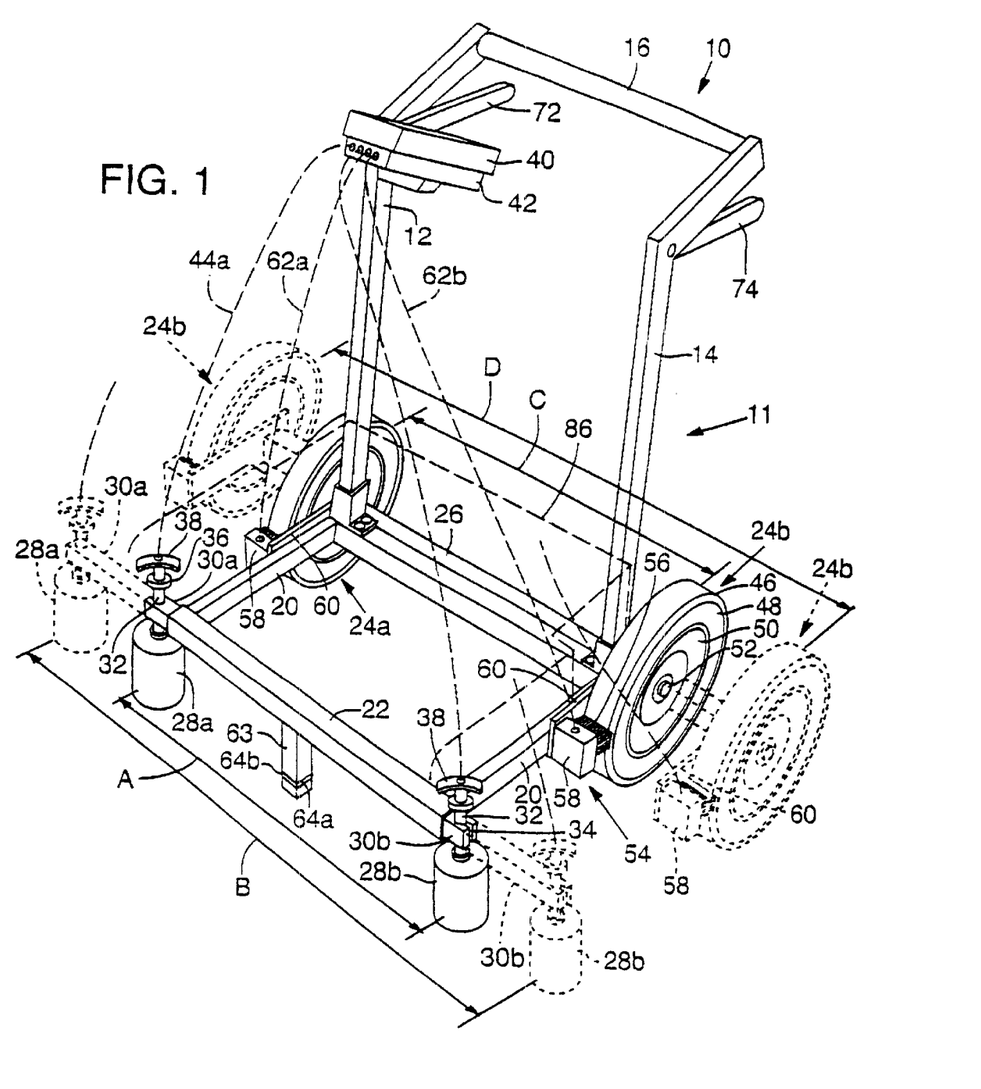
FIG. 1 is a partially schematic front perspective view showing an ESD testing apparatus according to the present invention and illustrating the extended positions of both the electrodes and the wheels in dashed lines.

A pair of electrodes 28a and 28b is mounted to forward transverse frame member 22 in a manner to allow the electrodes to be moveable between a first, retracted position (shown with the solid lines in FIG. 1) and a second, extended position (shown with the dashed lines in FIG. 1). One exemplary mechanism used to move the electrodes between the extended and retracted positions is described in detail below. In the preferred embodiment, electrode 28a is mounted to the outboard end of a rod 30a that is slidably received in frame member 22, which is hollow. Electrode 30b is likewise mounted to the outboard end of a separate rod 30b that is slidably received in the opposite end of frame member 22.

Figures 2A, 2B, 3:
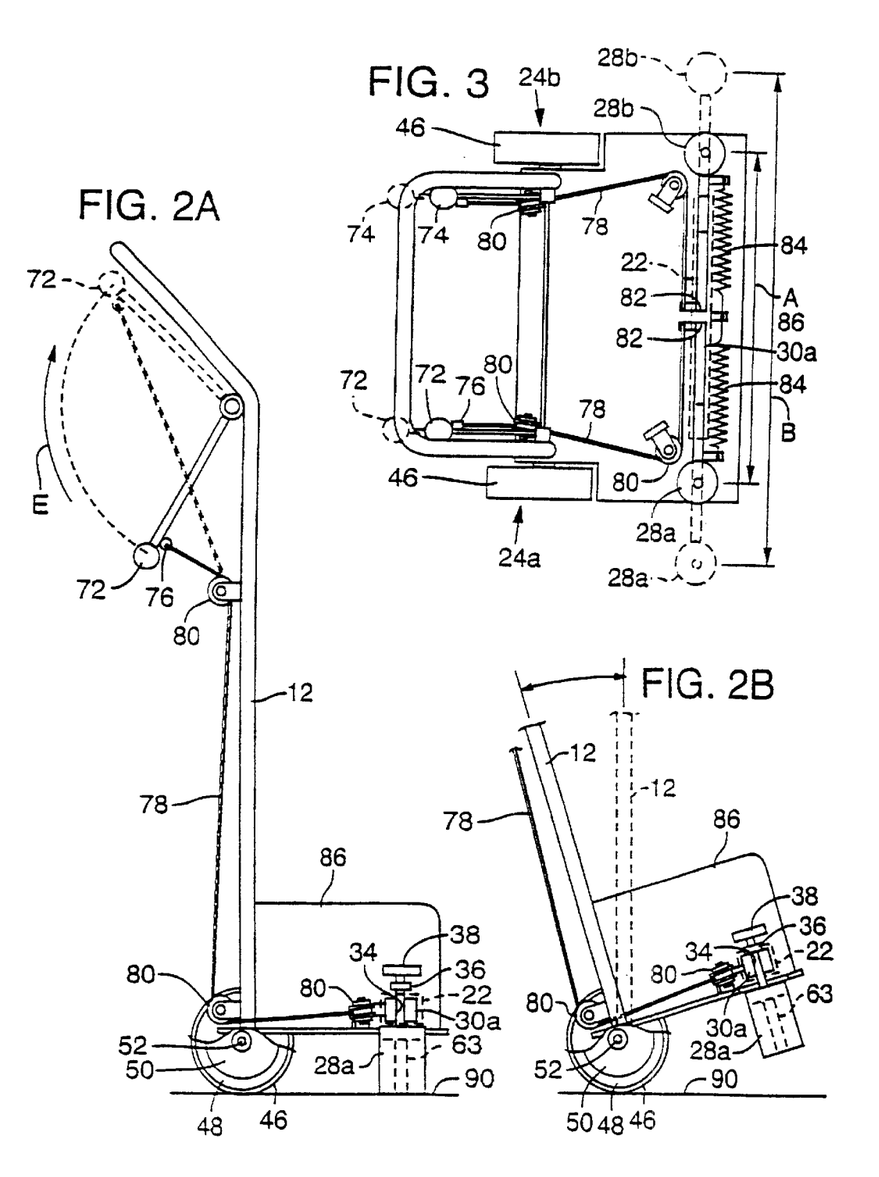
FIG. 2A is a schematic side view of the apparatus shown in FIG. 1, illustrating one possible linkage mechanism for moving the electrodes from the retracted position to the extended position, and showing the apparatus in the resting or "electrode-down" position with the electrodes resting on a surface.
FIG. 2B is a schematic side view of similar to FIG. 2B is a to view of the illustrating of FIG. 2A showing the apparatus rocked back on its wheels with the electrodes raised off the surface into the "electrode-up" position.
FIG. 3 is a top view of the apparatus of FIG. 2A.

Each electrode 28 is identical and comprises an industry standard electrode used for ESD testing in compliance with standards (see e.g. ANSI/ESD-S7.1-1994, above). However, the electrodes have been modified for use with the present invention. The electrodes are typically relatively heavy, about 5 lbs. each. The electrodes 28 are mounted to rods 30 to be readily removable from the rods. Moreover, the electrodes are mounted such that the electrodes are freely movable in their mounts in a vertical direction (relative to the ground plane). Specifically, a rod 32 extends upwardly from electrode 28a. Rod 32 is received in a cooperative slot 34 formed in the outermost end of rod 30. For reasons detailed below, rod 32 may be freely slid in slot 34 in the vertical direction. A retainer ring 36 is fixed to rod 32 to stop the sliding movement of electrode 28 in the down ward direction when apparatus 10 is tilted back as shown in FIG. 2B. A handle 38 is affixed to the upper end of rod 32 to facilitate easy manipulation of the electrode.

Each electrode 28 is electrically interconnected to an ohmmeter 40 through a switch box 42. Ohmmeter 40 and switchbox 42 are conveniently mounted on frame 12 in a position that allows an operator to easily read the ohmmeter and operate the switchbox. The leads between electrodes 28a and 28b are shown in dashed lines in FIG. 1, and are identified with reference numbers 44a and 44b, respectively. In practice the leads may be routed internally through the hollow frame members and the like if desired, in which case the leads may be coiled to allow for the electrodes to be extended away from the slots 34 for bench top measurements as described below.

Each wheel 24a and 24b is identical in construction. Importantly, each wheel is designed to be electrically conductive to act as an electrode for measuring the resistance between the wheels as apparatus 10 is being wheeled around a facility. The wheels thus act as electrodes when in a selected mode, described below. In a preferred embodiment the outer surface of each wheel is coated with an electrically conductive coating layer 46. There are numerous coating materials that may be used to provide layer 49; preferably the coating selected is highly conductive. Exemplary coating materials that may be used include conductive silicon coatings available from commercial sources such as Chomerics North America division of Parker Hannifin Corporation, Woburn, Mass. (www.chomerics.com), and conductive rubber coating materials. The coating material is chosen to be relatively soft and the wheels are chosen to be of a size so that the size of the surface contact area between the wheel and the surface upon which the wheel rests approximates the size of the surface contact area between an electrode 28 and the surface upon which it rests. This helps standardize the results of testing with wheels to the results of testing with electrodes 28. In addition to a wheel coated with an electrically conductive material as just described, the wheels themselves may be electrically conductive without additional coating materials or layers.

Conductive coating layer 46 is the only part of the wheels 24 that comes into contact with the surface on which the wheels are resting, or rolling over. Beneath layer 46, each wheel comprises a tire 48 and, radially inwardly of the tire, an insulating hub 50. Each wheel is rotatably connected to frame 26 with a suitable connection such as a bolt 52. Insulating hub 52 helps to eliminate any electrical interference between the frame and the conductive layer 46.

A brush assembly 54 facilitates the electrical connection between coating layer 46 and ohmmeter 40. Brush assembly 54 includes an electrically conductive wire brush 56 mounted to a bracket 58. Bracket 58 is mounted to an arm 60 that is mounted to frame 26 so that the brush assembly moves in unison with wheels 24 as they are moved laterally from the retracted position to the extended position, as illustrated in FIG. 1. Wire brush 56 is in physical and electrical contact with conductive coating layer 46 on wheel 24, and is electrically connected to ohmmeter 40 with an electrical lead 62. The lead 62 associated with wheel 24a is identified with reference number 62a and the lead 62 associated with wheel 24b is identified with reference number 62b. Each lead 62 extends from the brush assembly 58 to switch box 42. As noted above, the leads may be internally routed if desired.

The electrical connection between wire brush 56 and the ohmmeter has been found to be an highly effective in terms of the conductivity between the two. Stated otherwise, the connection between the wheel coating and the brush is an efficient way to obtain a reading of the conductivity of the floor when the wheel is acting as the electrode. It is to be appreciated that there are other ways to make an electrical connection between the conductive coating layer 46 and the ohmmeter 40, including for example electrically conductive bushings, brushes, rollers and the like.

A pressure foot 63 is connected to transverse frame member 22 and extends downwardly therefrom. As described in detail below, pressure foot 63 includes a pair of pressure activated electrical switches 64a and 64b, the function of which are detailed below.

As noted previously, electrodes 28 and wheels 24 may be moved between extended positions and retracted positions. These relative positions are illustrated in FIG. 1 with dashed lines. Although the wheels and electrodes may be manually moved between these two positions, in the preferred embodiment apparatus 10 includes a mechanical linkage that allows the wheels and the electrodes to be independently moved. There are numerous mechanical linkages that may be used to facilitate such movement, and those skilled in the art will readily appreciate that any suitable mechanism will suffice. Nonetheless, one specific mechanical linkage is detailed in FIGS. 2A and 3 for movement of electrodes 28 between the retracted and extended positions. That linkage will now be described.

Referring to FIG. 2A, a handle 72 is pivotally connected on one end to frame member 12 in a position such that an operator may grasp the handle to actuate it. Similarly, a handle 74 is pivotally connected to frame member 14. A first end 76 of a cable 78 is connected to handle 72 near the outermost end of the handle. Cable 78 is routed through pulleys 80 and the opposite end 82 of the cable is connected to rod 30a, which as noted earlier mounts electrode 28a and is slidable in frame member 22. A spring 84 has one end connected to a spring bracket 86 and the second end connected to rod 30a such that the spring normally biases the rod toward the retracted position shown in FIGS. 1 and 3 in solid lines. Handle 74 is connected to electrode 28b in an identical manner.

It will be appreciated that when apparatus 10 is in a resting state, electrodes 28a and 28b are biased by springs 84 into the retracted position. The separation between the electrodes in this position is identified as distance A in FIGS. 1 and 3. Utilizing the linkage mechanism just described, each electrode 28 may be moved outwardly independent of the other by pulling on the associated handle 72 or 74 as illustrated in FIG. 2A by arrow E. This motion pulls cable 78 against the biasing pressure of spring 84, causing electrode 28a to be moved laterally outwardly to the extended position. While each electrode may be moved independent of the other with the linkage described above, the handles 72 and 74 may be interconnected such that they move in unison, and in which case the electrodes move in unison between the retracted and extended positions. In either case, a latch (not shown) may be used to retain handle 72 in the position shown in FIG. 2A to maintain electrode 28a in the extended position. The separation between the electrodes in the extended position is identified as distance B in FIGS. 1 and 3. In the preferred embodiment, distance B is configured to comply with the separation specified in industry standard testing routines. Published ESD testing routines from ANSI specify a separation between electrodes of 3 feet. The electrodes may be held in the extended position with by latching the handles in the position shown in dashed lines in FIG. 2A. When such a latch is released, the springs 84 automatically retract the electrodes into the retracted position.

Wheels 24 also are movable between a retracted position and an extended position. Although not shown in the figures, a mechanical linkage such as that described above with reference to movement of the electrodes is used to control movement of the wheels. The wheels are moved with a linkage mechanism that is independent of the electrodes. Accordingly, the wheels and the electrodes are movable between the extended and retracted position independently of the other. The separation between the wheels in the retracted position is identified as distance C in FIG. 1, and the separation between the wheels in the extended position is identified as distance D.

It is beneficial to include a toolbox with apparatus 10 since various tools are commonly used in ESD testing and subsequent repair. As such, a toolbox 86 is schematically shown in the figures.

As stated previously, electrodes 28 are made be slid in the vertical direction relative to the ground plane in slots 34 of rod 30. Referring to FIG. 2A, which shows apparatus 10 in an "electrode-down" position, electrode 28a is resting on surface 90. In this electrode-down position, pressure foot 63 also rests on surface 90 so that frame 11 is resting on the triangle defined by wheels 24a and 24b, and pressure foot 63. Electrode 28a, however, rests on surface 90 only under its own weight by virtue of the electrode being slidable in slot 34. This may be seen by retainer ring 36, which in the electrode-down position of FIG. 2 is separated from the upper surface of rod 30a. The electrode must be supported on surface 90 only under its own weight because the published standard testing routines specify electrode weight to be used for a standard test. With the apparatus described, the test complies with industry standards because the electrode is supported by only its own weight in the electrode-down position, and the electrodes in the extended position are separated by industry standard distance.

The "electrode-up" position is shown in FIG. 2B. In this position the apparatus is tipped onto wheels 24, akin to the way a common hand truck is tipped onto its wheels. In the electrode-up position, the electrodes 28 slide downwardly in slots 34 under their own weight until retainer rings 36 abut rod 30a to arrest the downward movement of the electrodes.

Modes of Operation

The various ESD testing modes will now be described. Apparatus 10 is operable in three different operating modes. Several different testing routines may be run within each mode. The three basic operating modes are identified as "electrode," "wheel," and "automatic."

Figure 4:
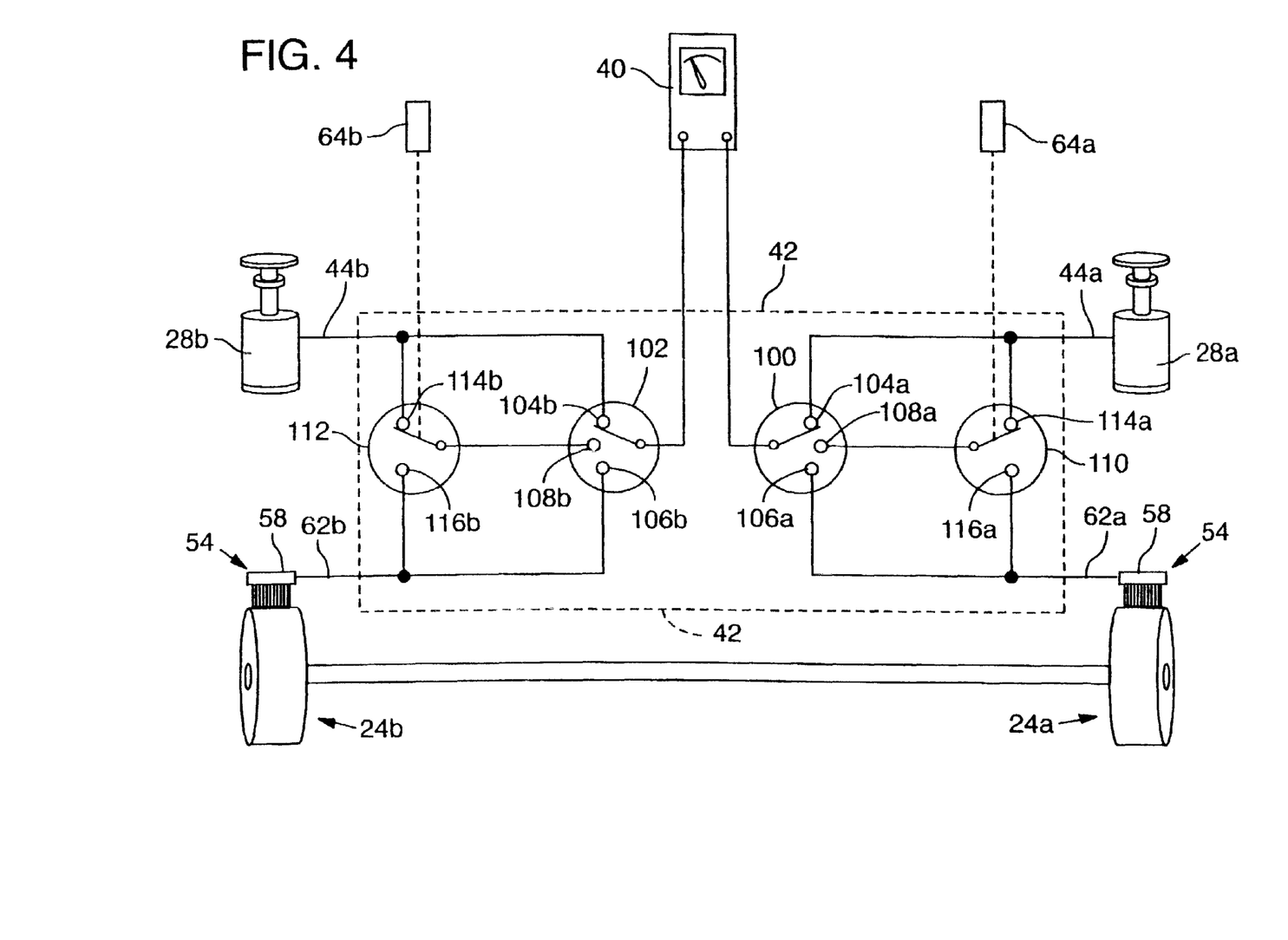
FIG. 4 is a schematic diagram illustrating exemplary electrical interconnections of the ESD testing apparatus according to the present invention.

The electrical connections of apparatus 10 are shown schematically in FIG. 4. Ohmmeter 40 is a standard ohmmeter with appropriate range calibrations to comply with the ESD testing described herein. The ohmmeter is electrically connected between a first switch 100, which switches electrode 28a, wheel 24a and pressure switch 64a, and a second switch 102, which switches electrode 28b, wheel 24b and pressure switch 64b. Each switch 100, 102 is a three-pole switch that may be manually manipulated by an operator at a external switch lever (not shown) in three different modes corresponding to the three operating modes identified above: electrode, wheel and automatic.

With reference to switch 100, the electrode mode is identified with position 104a, the wheel mode is identified with position 106a, and the automatic mode is identified with position 108a. Likewise, the three modes of switch 102 are the electrode mode, identified with position 104b, the wheel mode, identified with position 106b, and the automatic mode, identified with position 108b. When a switch 100 or 102 is in the automatic mode 108 a connection is made with a secondary switch 110 or 112, respectively. Switches 110 and 112 are identical two pole switches activated by the pressure switch 64a and 64b, respectively. Thus, when in the automatic mode and pressure switch 64a is closed, switch 110 makes contact with the electrode position 114 to complete a circuit from the electrode 28a to the ohmmeter 40. Likewise, when in the automatic mode and switch 64a is open, switch 110 makes contact with wheel position 116 to complete a circuit from the wheel 24a to the ohmmeter.

It will be recognized by those of ordinary skill in the art that multiple ESD testing routines are available with the present invention. A few of the many possibilities will be detailed.

An ESD test according to ANSI standards measures the resistance between electrodes 28a and 28b when a prescribed distance separates them, which is the distance B of FIGS. 1 and 3 when the electrodes are in the extended position. This testing is done with switches 100 and 102 in the electrode position 104a, 104b, respectively. The apparatus 10 is wheeled to a location to be tested. Often the apparatus is wheeled through doors and into relatively tight spaces. It may be advantageous during transport to leave the electrodes in the retracted position to facilitate movement of the apparatus, and to avoid damaging the electrodes. Once in the desired location, if the electrodes are not in the extended position already they are moved to the extended position and the apparatus is tipped into the electrode-down position shown in FIG. 2A. The resistance between the electrodes is then read at ohmmeter 40 and the apparatus may be wheeled to the next location to be tested. It should be noted, as well, that ANSI testing protocols require other preparations in addition to those described.

The electrical resistance between electrodes 28a and 28b may also be tested with the electrodes in the retracted position. This might be done, for example, when the test is run in a tight location where there is no room to separate the electrodes by the industry standard separation.

Continuing in the electrode mode, one or both electrodes may be easily removed from slot(s) 34 to run a floor to bench top test, or a point-to-point test on a bench top. As yet another alternative, one of the electrode leads, for example lead 44b, may be attached to ground and an electrode to ground test may be conducted by measuring the resistance between electrode 28a and ground.

In wheel mode 106 the ESD potential of a surface may be tested on a continuous basis as the apparatus is wheeled over the surface. This may be done with the wheels either in the extended position, where the separation between the wheels complies with industry standards for electrodes, or in the retracted position. In this mode the electrical resistance is measured between the wheels as they travel over a surface.

Although industry standards to date do not contemplate continuous testing as described herein, it has been found that there is a strong correlation and reproducibility between the results of continuous testing in wheel mode 106 and point to point testing in the electrode mode 104 as described above. As such, ESD testing in wheel mode 106 has been found to provide an accurate and reliable method of testing ESD potential for a large surface area, albeit the test method does not comply with existing standards. Nonetheless, if a potential problem area is identified though a test run in wheel mode 106, a standard point-to-point test may be run at that area with electrode mode 104.

Apparatus 10 allows the operator to test the conductivity between one wheel and one electrode. For this mode of operation one switch 100 or 102 is placed in the electrode mode and the other is placed in the wheel mode. By way of example, switch 100 may be placed in electrode mode 104a and switch 102 is placed in wheel mode 106b. The operator may then easily run bench to floor ESD measurements by placing electrode 28a on a bench top (or other surface). The measurement thus obtained correlates to the ESD potential between the floor surface (measured at wheel 24b) and the bench top (measured at electrode 28a).

In the automatic mode 108, apparatus 10 measures the conductivity between wheels 24 when the apparatus is in the electrode-up position (FIG. 2B) and automatically switches to the electrode mode when the apparatus is in the electrode-down position (FIG. 2A). For the automatic mode both switches 100 and 102 are moved to automatic mode 108a, and 108b, respectively. In this mode the circuit from switches 100 and 102 runs through secondary switches 110 and 112. These switches are controlled by pressure switches 64a and 64b, which as noted above reside in pressure foot 63. Specifically, if both switches 100 and 102 are in the automatic mode and apparatus 10 is in the electrode-down position of FIG. 2A, then pressure switches 64a and 64b close to thereby close the circuit between electrodes 28a and 28b by closing the connection at 114a, and 114b, respectively, thereby completing the circuit between the electrodes 28 and ohmmeter 40. When apparatus 10 is tilted into the electrode-up position of FIG. 2B, switches 64a and 64b open and switches 110 and 112 make contact with the wheel connections at 116a and 116b, thereby completing the circuit between wheels 24 and ohmmeter 40. Of course, the automatic mode functions the same regardless of whether the electrodes and/or wheels are in the retracted or extended positions. Moreover, one switch 100 or 102 may be placed in the automatic mode 108 while the other switch is in one of the other modes.

Finally, point to ground measurements may be taken by disconnecting a lead from one electrode (or wheel) and connecting the lead to ground. The appropriate switch connections are then made to test between the selected test points.

Alternate Embodiments

Figure 5:
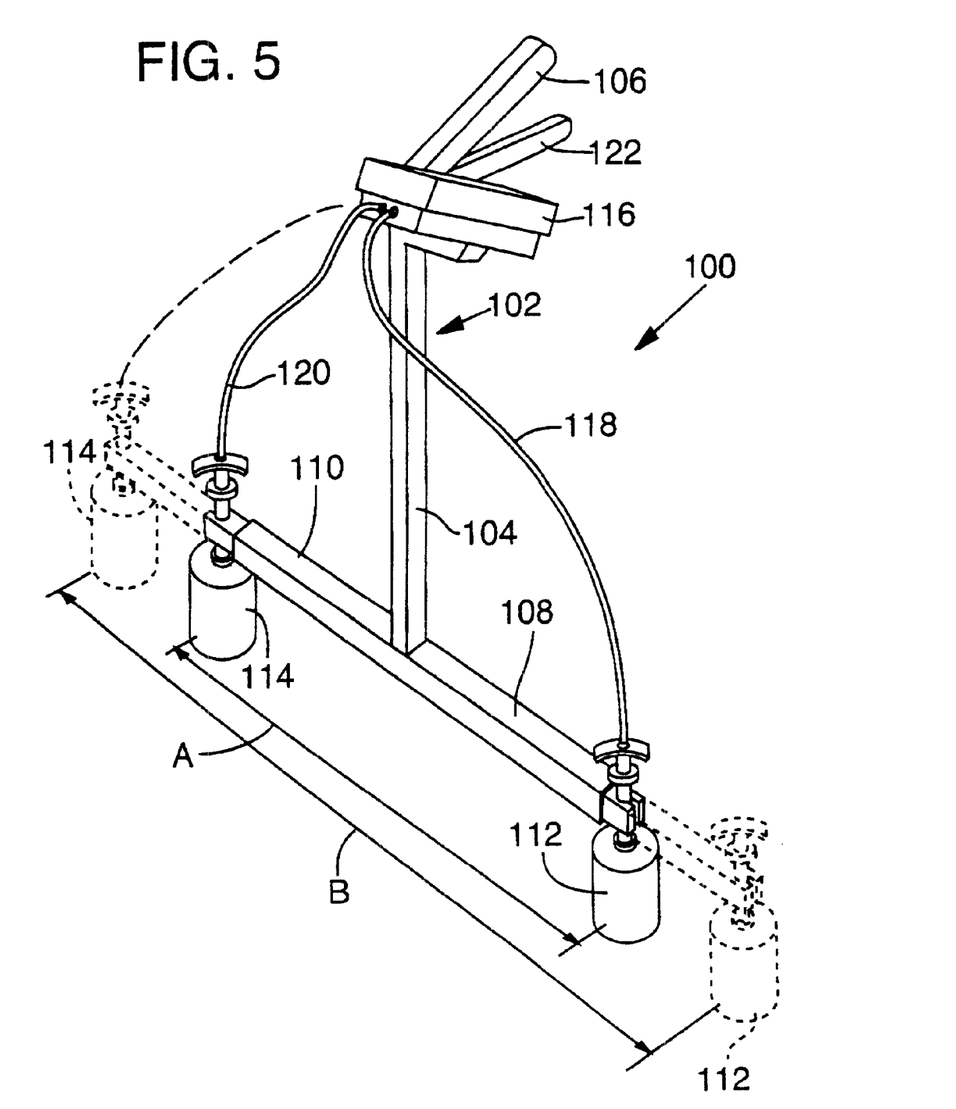
FIG. 5 is a partially schematic front perspective view of an alternative embodiment of an ESD testing apparatus according to the present invention.

An alternate embodiment of an ESD testing apparatus 100 according to the present invention is illustrated in FIG. 5. Apparatus 100 is similar to apparatus 10 described in detail above, except that apparatus 100 lacks wheels by which to move the apparatus from place to place. Nonetheless, apparatus 100 provides an easy method to transport the ESD testing electrodes from one testing location to the next by providing an easily transported frame for the electrodes.

Apparatus 100 comprises a frame assembly 102 having an upright member 104 with a handle 106 at the upper end thereof, and opposed lateral extension arms 108, 110 connected to the lower end of the upright member. An electrode 112 is removably mounted to the outer end of extension arm 108 in a manner identical to the manner in which the electrodes 28 are mounted with respect to apparatus 10, as described in detail above. An electrode 114 is identically removably mounted to the outer end of extension arm 110. An ohmmeter 116 is mounted to upright member 104 in a location so that the operator may easily read the meter. Ohmmeter 116 is electrically connected between electrodes 112 and 114 with leads 118, 120, respectively.

The separation distance between the electrodes may be fixed at any desired distance, preferably although not necessarily at the separation distance specified in industry standards. Alternately, apparatus 100 may include a handle 122 having a linkage as described above but not shown in FIG. 5 to move the electrodes between a first retracted position (in which the electrodes are separated by distance A) and a second, extended position (distance B). In the later case the distance separating the electrodes in the retracted position would be less than standard separation, and the distance B would be compliant with industry standards.

As noted, the electrodes are mounted in the same manner as described above. As such, the electrodes are movable in the vertical direction (relative to the ground plane) with respect to the laterally extending arms 108, 110 so that when testing is being run, the electrodes are supported on the test surface under only their own weight. One or more support feet (not shown) may be added to the frame 102 to stabilize the frame during testing so that the frame is self-supporting.

Since the electrodes may be removed from their mounts in extension arms 108, 110, it will be appreciated that the apparatus 100 is capable of point to point testing on a floor or bench top, floor to bench top testing, point to ground testing, etc.

While the present invention has been described in terms of a preferred embodiment and certain alternatives, it will be appreciated by one of ordinary skill that the spirit and scope of the invention is not limited to those embodiments, but extend to the various modifications and equivalents as defined in the appended claims.

I claim:

1. An ESD testing apparatus, comprising:

a frame;

a pair of wheels rotatably mounted to the frame such that said wheels support said frame and allow said frame to be moved on said wheels;

a first electrode mounted to the frame;

a second electrode mounted to the frame;

an ohmmeter electrically connected between the first and second electrodes;

the first and second electrodes movable between a retracted position where the electrodes are held in a first spaced apart relationship and an extended position where the electrodes are held in a second spaced apart relationship, and wherein the separation between the electrodes in the second spaced apart relationship complies with industry standard ANSI/ESD-S7.1-1994 for electrode separation.

2. A The ESD testing apparatus of claim 1 wherein the wheels comprise the electrodes.

3. The ESD testing apparatus of claim 1 wherein the electrodes are separate from the wheels.

4. The ESD testing apparatus of claim 1 including an electrical circuit operable in a first mode in which the wheels define the electrodes and a second mode in which the electrodes are separate from the wheels.

5. The ESD testing apparatus of claim 1 wherein the electrodes are mounted in respective first and second electrode mount members connected to the frame and the frame is movable between an electrode-down position wherein the electrodes are supported by their own weight on a test surface and an electrode-up position wherein the electrodes are separated from the test surface.

6. The ESD testing apparatus of claim 5 wherein when the frame is in the electrode-up position the wheels define the electrodes, and including an electrical circuit operable when the frame is in the electrode-up position to measure conductivity between the wheels.

7. The ESD testing apparatus of claim 6 wherein when the frame is in the electrode-down position the electrodes are separate from the wheels, and including an electrical circuit operable when the frame is in the electrode-down position to measure conductivity between the electrodes.

8. The ESD testing apparatus of claim 7 including an electrical circuit operable to automatically measure the conductivity between the wheels when the apparatus is in the electrode-up position and measure the conductivity between the electrodes when the apparatus is in the electrode-down position.

9. The ESD testing apparatus of claim 1 wherein the electrodes are removable from the frame to be remotely positioned from the frame.

10. The ESD testing apparatus of claim 1 wherein each wheel is electrically conductive.

11. The ESD testing apparatus of claims 10 wherein the electrically conductive wheel comprises a silicone coating material.

12. A mobile ESD testing apparatus, comprising:
a frame having a pair of wheels for supporting said frame and for moving said frame on said wheels;
a first electrode mounted to the frame;
a second electrode mounted to the frame;
an ohmmeter electrically connected between the first and second electrodes; and wherein said wheels define said electrodes.

13. The ESD testing apparatus of claim 12 wherein the first and second electrodes are movable between a retracted position where the electrodes are held in a first spaced apart relationship and an extended position where the electrodes are held in a second spaced apart relationship.

14. The ESD testing apparatus of claim 12 where the electrodes are separate from the wheels.

15. A method of testing the ESD potential of a test surface, comprising the steps of:
(a) mounting first and second electrodes on a wheeled frame in a first spaced apart relationship and such that said wheeled frame may be moved from a first location to a second location by moving said wheeled frame on wheels;
(b) orienting the frame so that the electrodes are in physical and electrical contact with the test surface; and
(c) measuring the electrical resistance between the electrodes.

16. The method of claim 15 wherein the wheels define the electrodes.

17. The method of claim 16 wherein the measuring step is done while the frame is being moved on the wheels.

18. The method of claim 15 wherein the electrodes are movable between a retracted position and an extended position, and wherein the separation between the electrodes in the extended position complies with ANSI/ESD-S7.1-1994.

19. An ESD testing apparatus, comprising:
a frame;
a pair of wheels rotatably mounted to the frame;
a first electrode mounted to the frame;
a second electrode mounted to the frame;
an ohmmeter electrically connected between the first and second electrodes;
the first and second electrodes mounted in respective first and second electrode mount members connected to the frame and the frame is movable between an electrode-down position wherein the electrodes are supported by their own weight on a test surface and an electrode-up position wherein the electrodes are separated from the test surface;
wherein the electrodes are movable between a retracted position where the electrodes are held in a first spaced apart relationship and an extended position where the electrodes are held in a second spaced apart relationship.

20. The ESD testing apparatus of claim 19 wherein when the frame is in the electrode-up position the wheels define the electrodes, and including an electrical circuit operable when the frame is in the electrode-up position to measure conductivity between the wheels.

21. A method of testing the ESD potential of a test surface, comprising the steps of:
(a) mounting first and second wheeled electrodes on frame in a first spaced apart relationship such that said frame may be moved from a first location to a second location by moving said frame on said wheeled electrodes;
(b) orienting the frame so that the electrodes are in physical and electrical contact with the test surface; and
(c) measuring the electrical resistance between the electrodes as said frame is being moved on said wheeled electrodes.

22. An ESD testing apparatus, comprising:
a frame;
a pair of wheels rotatably mounted to the frame such that said wheels; said frame and allow said frame to be moved on said wheels;
a first electrode mounted to the frame;
a second electrode mounted to the frame;
an ohmmeter electrically connected between the first and second electrodes;
the first and second electrodes movable between a retracted position where the electrodes are h&d in a first spaced apart relationship and an extended position where the electrodes are held in a second spaced apart relationship; and
wherein the wheels define the electrodes.

23. An ESD testing apparatus comprising:
a frame;
pair of wheels rotatably mounted to the frame such that said wheels support said frame and allow said frame to be moved on said wheels;

a first electrode mounted to the frame;

a second electrode mounted to the frame:

an ohmmeter electrically connected between the first and second electrodes;

the first and second electrodes movable between a retracted position where the electrodes are held in a first spaced apart relationship and an extended position where the electrodes are held in a second spaced apart relationship; and an electrical circuit operable in a first mode in which the wheels define the electrodes and a second mode in which the electrodes are separate from the wheels.

24. The ESD testing apparatus of claim 23 wherein the electrodes are mounted in respective first and second electrode mount members connected to the frame and the frame is movable between an electrode-down position wherein the electrodes are supported by their own weight on a test surface and an electrode-up position wherein the electrodes are separated from the test surface.

25. The ESD testing apparatus of claim 24 wherein when the frame is in the electrode-up position the wheels define the electrodes, and including an electrical circuit operable when the frame is in the electrode-up position to measure conductivity between the wheels.

26. The ESD testing apparatus of claim 25 wherein when the frame is in the electrode-down position the electrodes are separate from the wheels, and including an electrical circuit operable when the frame is in the electrode position to measure conductivity between the electrodes.

27. The ESD testing apparatus of claim 26 including an electrical circuit operable to automatically measure the conductivity between the wheels when the apparatus is in the electrode-up position and measure the conductivity between the electrodes when the apparatus is in the electrode-down position.

* * * * *